United States Patent
Kovi et al.

(10) Patent No.: US 11,260,065 B2
(45) Date of Patent: Mar. 1, 2022

(54) STORAGE-STABLE READY-TO-USE INJECTABLE FORMULATIONS OF THIOTEPA

(71) Applicant: RK Pharma Solutions LLC, Piscataway, NJ (US)

(72) Inventors: Ravishanker Kovi, Monroe Township, NJ (US); George Roby Thomas, Winnipeg (CA); Nirmal Chaitanya Indravadanbhai, Gujarat (IN); Patel Mitesh Manubhai, Gujarat (IN); Thupalli Ajeykumar Reddy, Bangalore (IN); Jayaraman Kannappan, Vadodara (IN)

(73) Assignee: RK Pharma Solutions LLC, Piscataway, NJ (US)

( * ) Notice: Subject to any disclaimer, the term of this patent is extended or adjusted under 35 U.S.C. 154(b) by 142 days.

(21) Appl. No.: 16/690,696

(22) Filed: Nov. 21, 2019

(65) Prior Publication Data

US 2020/0163979 A1    May 28, 2020

Related U.S. Application Data

(60) Provisional application No. 62/772,220, filed on Nov. 28, 2018.

(51) Int. Cl.
*A61K 31/675* (2006.01)
*A61K 9/00* (2006.01)

(52) U.S. Cl.
CPC .......... *A61K 31/675* (2013.01); *A61K 9/0019* (2013.01)

(58) Field of Classification Search
CPC ............................ A61K 31/675; A61P 35/00
See application file for complete search history.

(56) References Cited

PUBLICATIONS

Murray et al., Pharmacist, 1997, 54(22): 2588-91.*

* cited by examiner

*Primary Examiner* — Rei Tsang Shiao
(74) *Attorney, Agent, or Firm* — Antonio Papageorgiou; Lombard & Geliebter LLP

(57) ABSTRACT

A stable, ready-to-use injectable solution including thiotepa and one or more pharmaceutically acceptable solvents, co-solvents, and/or solubilizing agents. Formulations retain at least 90% and as high as 99% of the purity of thiotepa as measured by HPLC after storage at 25° C./60% RH for a period of 7 days. Certain formulations retain at least 99% of the purity of thiotepa as measured by HPLC after storage for at least six months at 2-8° C.

20 Claims, No Drawings

STORAGE-STABLE READY-TO-USE INJECTABLE FORMULATIONS OF THIOTEPA

CROSS-REFERENCE TO RELATED APPLICATIONS

This application claims the benefit of U.S. Provisional Patent Application No. 62/772,220 filed Nov. 28, 2018, the entirety of which is incorporated by reference herein.

FIELD OF THE INVENTION

The present invention relates to a stable, ready to use, injectable thiotepa formulation.

BACKGROUND OF THE INVENTION

Thiotepa, also known as tris(1-aziridinyl)phosphine sulfide, is an alkylating agent used to treat cancer. Thiotepa has the molecular formula $C_6H_{12}N_3PS$, and a molecular weight of 189.23, and it appears as fine, white crystalline flakes, with a melting range of 52° C. to 57° C. It is soluble in water and organic solvents. When reconstituted with sterile water for injection, the resulting solution has a pH of approximately 5.5 to 7.5. Thiotepa is unstable in acid medium. The structural formula is:

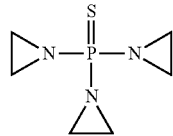 [SMILES: S=P(N1CC1)(N1CC1)N1CC1]

The commercial formulation of injectable thiotepa (TEPADINA®, Adienne s.r.l., Caponago, IT) is supplied as a nonpyrogenic, sterile lyophilized white powder for intravenous, intracavitary, or intravesical use after reconstitution and dilution. The 15 mg dosage form is reconstituted with 1.5 ml of sterile water and diluted in saline to a desired dose prior to administration. The 100 mg dosage form is reconstituted with 10 ml of sterile water and diluted in saline to a desired dose prior to administration.

TEPADINA® injectable thiotepa has disadvantages such as but not limited to high manufacturing cost and the requirement of complex processes and equipment. TEPADINA® injectable thiotepa also requires an additional step of reconstitution prior to administration. Improper reconstitution may sometimes result in failure to provide a clear solution.

SUMMARY OF THE INVENTION

The present invention provides a stable, ready-to-use injectable thiotepa solution which is easy to administer without need of any reconstitution step and has a desirable solubility, stability and safety profile.

In one or more embodiments there is provided a ready-to-use liquid parenteral formulation of thiotepa.

In one or more further embodiments, there is provided a storage-stable, ready-to-use, injectable liquid parenteral composition including thiotepa and one or more pharmaceutically acceptable solvents, co-solvents, and/or solubilizing agents.

In still further embodiments provided are ready-to-use liquid parenteral formulations including thiotepa, one or more pharmaceutically acceptable solvents, co-solvents, and/or solubilizing agents and at least one pharmaceutically acceptable excipient or adjuvant.

In one or more embodiments, disclosed is a ready to use, pharmaceutically acceptable injectable liquid formulation comprising thiotepa or a pharmaceutically acceptable salt thereof and at least one pharmaceutically acceptable solvent or co-solvent, wherein the formulation retains at least 90% of the purity of thiotepa as measured by HPLC after storage at 25° C./60% RH for a period of 7 days. In some embodiments the formulation retains at least 94% of the purity of thiotepa as measured by HPLC after storage at 25° C./60% RH for a period of 7 days. In still further embodiments the formulation retains at least 99% of the purity of thiotepa as measured by HPLC after storage at 25° C./60% RH for a period of 7 days. In still further embodiments, the formulation retains at least 99% of the purity of thiotepa as measured by HPLC after storage for at least six months at 2-8° C.

In some embodiments the formulation includes ethanol. In still other embodiments the formulation includes ethanol, propylene glycol and optionally one or more of a polymer and a solubilizing agent. For example, the formulation may include 100 mg thiotepa, 1-10 ml ethanol and 0-5 ml propylene glycol. In some embodiments the formulation includes 10 ml ethanol and 0 ml propylene glycol. The formulation may consist essentially of thiotepa and ethanol, or may consist of thiotepa and ethanol.

In still yet further embodiments the formulation may include ethanol, polyethylene glycol (PEG) and optionally one or more of a polymer and a solubilizing agent. The formulation may consist essentially of ethanol, polyethylene glycol (PEG), a polymer, a solubilizing agent, and a pH adjusting component so that the pH of the formulation is from 7.5 to 8.5.

In some embodiments, the formulation has a concentration of thiotepa of about 10 mg thiotepa per ml of the total amount of the solvent and/or co-solvent.

The storage-stable, ready-to-use, injectable compositions of the present invention are useful for the treatment of various types of cancer.

The details of one or more embodiments of the invention are set forth in the description below. Other features, objects and advantages of the invention will be apparent from the description.

DETAILED DESCRIPTION OF THE PREFERRED EMBODIMENTS

The present invention now will be described more fully hereinafter with reference to the accompanying examples and experiments, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, "thiotepa" refers to thiotepa and the pharmaceutically acceptable salts, solvates, hydrates and anhydrous forms thereof.

As used here in "ready-to-use" when used in connection with a thiotepa formulation refers to a formulation that includes thiotepa in dissolved or solubilized form and/or is intended to be used as such or upon further dilution in intravenous diluents.

As used herein, and unless otherwise specified, the term "storage-stable" refers to any thiotepa-containing composition or formulation having sufficient physical and chemical stability to allow storage at a convenient temperature, such as between about 0° C. and about 50° C., for a commercially reasonable period of time. The phrase "physical stability" refers to maintenance of colour or colourless state, dissolved oxygen level, head space oxygen level and particulate matter and the phrase "chemical stability" relates to formation of drug-related impurities in terms of total impurities, single maximum individual impurity, or maximum individual unknown impurity. For pharmaceutical products, stability is required for commercially relevant times after manufacturing, such as for about 6, 12, 18, 24, or 36 months, during which time a product is kept in its original packaging under specified storage conditions.

As used herein, and unless otherwise specified, the term "about" means an acceptable error for a particular value as determined by one of ordinary skill in the art, which depends in part on how the value is measured or determined. In certain embodiments, the term about means within 10%, 9%, 8%, 7%, 6%, 5%, 4%, 3%, 2%, 1%, 0.5%, 0.1%, or 0.05% of a given value or range.

In one or more embodiments, ready-to-use liquid parenteral formulations of thiotepa include thiotepa and one or more pharmaceutically acceptable solvents, co-solvents, and/or solubilizing agents. In other embodiments, ready-to-use liquid parenteral formulations of thiotepa include thiotepa, one or more pharmaceutically acceptable solvents, co-solvents, and/or solubilizing agents, and optionally, one or more pharmaceutically acceptable excipients or adjuvants.

Suitable pharmaceutically acceptable solvents include but are not limited to dimethylacetamide (DMA), dimethyl sulfoxide (DMSO), N-methylpyrolidone, dimethylisosorbide, ethanol, propylene glycol, glycerine, polyethylene alcohol, propylene glycol esters, polyethylene glycols and the like. Preferred solvents are dimethylacetamide (DMA), ethanol, polyethylene glycol (PEG), glycerine, benzyl alcohol and propylene glycol.

Suitable pharmaceutically acceptable co-solvents include but are not limited to ethanol, polyethylene glycol, glycerine and glycofurol.

Suitable pharmaceutically acceptable solubilizing agents include but are not limited to L-arginine, cyclodextrin derivatives, alpha-cyclodextrin, beta-cyclodextrin, for example, hydroxypropyl beta cyclodextrin (HPBCD), sulfobutylether-betacyclodextrin, randomly methylated beta-cyclodextrin and the like, gamma-cyclodextrin, modified alpha-cyclodextrin, modified beta cyclodextrin, modified gamma cyclodextrin or any combination thereof.

Pharmaceutically acceptable excipients or adjuvants include but are not limited to one or more preservatives, polymers, pH adjusting agents, isotonicity adjusting agents, surfactants, chelating agents and antioxidants.

Examples of pharmaceutically acceptable preservatives include but are not limited to chlorobutanol, benzalkonium chloride, methyl paraben, propyl paraben, benzoic acid, sodium benzoate, sorbic acid, benzethonium chloride, cetyl pyridinium chloride, benzyl bromide, benzyl alcohol, phenylmercury nitrate, phenylmercury acetate, thiomersal, merthiolate, chlorhexidine, phenylethyl alcohol, quaternary ammonium chloride, sodium benzoate, sodium propionate, etc. and combinations thereof.

Examples of pharmaceutically acceptable polymers include but are not limited to carbomer, polycarbophil, gellan gum, poloxamer 188, cellulose derivatives, acrylates, etc. and combinations thereof.

Examples of pharmaceutically acceptable pH adjusting agents include but are not limited to sodium hydroxide, hydrochloric acid, boric acid, citric acid, acetic acid, phosphoric acid, succinic acid, potassium hydroxide, ammonium hydroxide, magnesium oxide, calcium carbonate, magnesium carbonate, magnesium aluminum silicates, malic acid, potassium citrate, sodium phosphate, lactic acid, gluconic acid, tartaric acid, fumaric acid, diethanolamine, monoethanolamine, sodium carbonate, sodium bicarbonate, triethanolamine, etc. and combinations thereof.

Examples of pharmaceutically acceptable isotonicity adjusting agents include but are not limited to sodium chloride, potassium chloride, calcium chloride and magnesium chloride, glucose, glycerol, etc. and combinations thereof.

Examples of pharmaceutically acceptable surfactants include but are not limited to amphoteric, non-ionic, cationic and anionic molecules. For example, suitable surfactants include but are not limited to polysorbates, sodium lauryl sulfate, lauryl dimethyl amine oxide, docusate sodium, cetyl trimethyl ammonium bromide (CTAB), polyethoxylated alcohols, polyoxyethylene sorbitan, octoxynol, polyoxyl lauryl ether, Brij® surfactants (polyoxyethylene vegetable-based fatty ethers derived from lauryl, cetyl, stearyl and oleyl alcohols), bile salts (such as sodium deoxycholate and sodium cholate), polyoxyl castor oil, nonylphenol ethoxylate, lecithin, polyoxyethylene surfactants, polyethylene glycol esters, glycol esters of fatty acids, monoalkanolamine condensates, polyoxyethylene fatty acid amides, quaternary ammonium salts, polyoxyethylene alkyl and alicyclic amines, polyoxyethylene, sorbitan monolaurate, sorbitan stearate, Cremophor® (polyethoxylated castor oil), Solutol® (ethylene oxide/12-hydroxy stearic acid), tyloxapol, etc. and combinations thereof.

Pharmaceutically acceptable chelating agents include but are not limited to citric acid and derivatives thereof, for example, anhydrous citric acid and the like, ethylenediaminetetraacetic acid (EDTA), disodium EDTA or derivatives thereof, niacinamide or derivatives thereof, sodium deoxycholate or derivatives thereof, pentetic acid or derivatives thereof, etc. and combination thereof.

Examples of pharmaceutically acceptable anti-oxidants include but are not limited to butylated hydroxytoluene (BHT), butylated hydroxyanisole (BHA), propyl gallate (PG), monothioglycerol, ascorbic acid, sodium ascorbate, erythorbic acid, potassium metabisulfite, sodium metabisulfite, propionic acid, sodium formaldehyde sulphoxylate, reduced glutathione, thiourea, cysteine, n-acetlcysteine, methionine, sodium sulfite, alkyl gallate, vitamin E or other tocopherol analogs such as tocopherol acetate and TPGS, etc. and combinations thereof.

The formulations according to the present invention may be in the form of clear injectable solution, suspension or emulsion.

The ratio of thiotepa to the one or more pharmaceutically acceptable solvents and/or co-solvents may be from 100:1 to 1:100. In some embodiments the ratio of thiotepa to the one or more pharmaceutically acceptable solvents and/or co-solvents may be from 90:1 to 1:90. In still other embodiments the ratio of thiotepa to the one or more pharmaceutically acceptable solvents and/or co-solvents may be from 80:20 to 20:80. In some embodiments the ratio of thiotepa to the one or more pharmaceutically acceptable solvents and/or co-solvents may be from 70:30 to 30:70. In further embodiments the ratio of thiotepa to the one or more pharmaceutically acceptable solvents and/or co-solvents may be from 60:40 to 40:60. In still further embodiments the ratio of thiotepa to the one or more pharmaceutically acceptable solvents and/or co-solvents is 50:50.

In some embodiments the storage-stable ready-to-use injectable formulation may have a concentration of thiotepa of about 10 mg thiotepa per ml of the total amount of solvent and/or co-solvent. In other embodiments the storage-stable ready-to-use injectable formulation may have a concentration of thiotepa of less than 10 mg/ml of the total amount of solvent and/or co-solvent. In other embodiments the injectable formulation may have a concentration of thiotepa of from about 1 mg/ml to about 9 mg/ml of the total amount of solvent and/or co-solvent. In another embodiment the injectable formulation may have a concentration of thiotepa of from about 3 mg/ml to about 7 mg/ml of the total amount of solvent and/or co-solvent. In other embodiments the injectable formulation may have a concentration of thiotepa of about 5 mg/ml of the total amount of solvent and/or co-solvent. In other embodiments the concentration of thiotepa in the formulation may be less than about 5 mg/ml of the total amount of solvent and/or co-solvent. In still other embodiments the concentration of thiotepa in the formulation may be about 1 mg/ml of the total amount of solvent and/or co-solvent. In still further embodiments the injectable formulation may have a concentration of thiotepa of from about 0.001 w/v to about 0.1 w/v of the total amount of solvent and/or co-solvent. In still further embodiments the injectable formulation may have a concentration of thiotepa of from about 0.04 w/v to about 0.08 w/v of the total amount of solvent and/or co-solvent. In still further embodiments the injectable formulation may have a concentration of thiotepa of about 0.05% w/v of the total amount of solvent and/or co-solvent.

In some embodiments storage-stable ready-to-use injectable formulations disclosed herein include 100 mg thiotepa, 1-10 ml ethanol, 0-5 ml propylene glycol, and optionally a polymer, a solubilizing agent, and/or a pH adjusting component so that the pH of the formulation is from 7.5 to 8.5. In still other embodiments storage-stable ready-to-use injectable formulations disclosed herein include 100 mg thiotepa, 1-10 ml ethanol, 0-5 ml polyethylene glycol, and optionally a polymer, solubilizing agent and/or a pH adjusting component so that the pH of the formulation is from 7.5 to 8.5.

In some embodiments storage-stable ready-to-use injectable formulations disclosed herein include 15 mg thiotepa, 0.15-1.5 ml ethanol, 0-0.75 ml propylene glycol, and optionally a polymer, a solubilizing agent, and/or a pH adjusting component so that the pH of the formulation is from 7.5 to 8.5. In still other embodiments storage-stable ready-to-use injectable formulations disclosed herein include 100 mg thiotepa, 0.15-1.5 ml ethanol, 0-0.75 ml polyethylene glycol, and optionally a polymer, solubilizing agent and/or a pH adjusting component so that the pH of the formulation is from 7.5 to 8.5.

The storage-stable, ready-to-use injectable thiotepa-containing formulations disclosed herein do not require any additional reconstitution step at the time of administration.

The formulations have a controlled impurity profile suitable for regulatory approval at various storage conditions. For example, and not by way of limitation, the storage-stable ready-to-use thiotepa formulations may be stored at 25° C. By way of further example, the storage-stable, ready-to-use thiotepa formulations may be stored at 2-8° C. The storage-stable, ready-to-use thiotepa formulations for injection may retain at least 90% of the potency of thiotepa after storage for six months at 25° C. temperature and 60% relative humidity. In some embodiments the storage-stable, ready-to-use thiotepa formulations for injection may retain at least 90% of the potency of thiotepa after storage for six months at 2-8° C. In various embodiments the storage-stable, ready-to-use thiotepa formulations for injection may retain at least 99% of the purity of thiotepa as measured by HPLC after storage for at least six months at 2-8° C. In other embodiments the storage-stable, ready-to-use thiotepa formulations for injection may retain at least 99% of the purity of thiotepa as measured by HPLC after storage at 25° C./60% RH for a period of 7 days.

The storage stable, ready-to-use, injectable formulations may be formulated to provide single or multiple dosage administration. The single dosage formulation may be packaged in an ampoule, a vial, or a syringe. Multiple dosage formulations may be packaged in a vial. Multiple dosage formulations may preferably include at least one preservative.

The formulations have a pH value from about 4 to about 9. In some embodiments the pH range is from about 7.0 to about 9.0. In other embodiments the pH is about 8.5.

Storage-stable ready-to-use, injectable formulations disclosed herein contain thiotepa having a purity of from about 80% to about 120%. In some embodiments the formulation contains thiotepa having a purity of from about 90% to about 110%. In some embodiments the formulation contains thiotepa having a purity of about 100%.

Formulations as disclosed herein are useful in the treatment of various types of cancer, including adenocarcinoma of the breast, ovary and urinary bladder, and lymphomas such as non-Hodgkins lymphosarcoma and Hodgkin's disease. Methods of treatment of such cancers are disclosed including administering to an individual in need thereof a therapeutically effective amount of a storage stable, ready-to-use, injectable formulation as disclosed herein.

EXAMPLES

The following examples are for the illustration only and are not intended in any way to limit the scope of the present invention. All purity and impurities data reflect analysis by HPLC as described hereinbelow.

Example 1A

TABLE 1

| Ingredients | Qty/vial |
|---|---|
| Thiotepa | 100 mg |
| Ethanol | 10 ml |

Using the ingredients in Table 1, thiotepa was added to a manufacturing vessel containing ethanol and the mixture was stirred to obtain a clear solution. The obtained solution was filtered and filled in vials, followed by capping and sealing of the vials. The formulation was tested for stability at 25° C./60% RH for a period of 7 days. Stability data is summarized in Table 1A.

TABLE 1A

| Stability at Day 7 | RRT | Day 7 |
|---|---|---|
| Purity | | 99.78% |
| Maximum Individual Impurity | 1.36 | 0.19% |
| Total Impurities | | 0.22% |

Example 1B

Using the ingredients in Table 1, thiotepa was added to a manufacturing vessel containing ethanol and the mixture stirred to obtain a clear solution. The obtained solution was filtered and filled in vials, followed by capping and sealing of the vials. The formulation was tested for stability at 2-8° C. for a period of 8 months. Stability data is summarized in Table 1B.

TABLE 1B

| Stability at 8 Months | RRT | 8 Months |
|---|---|---|
| Purity | | 99.50 |
| Maximum Individual Impurity | 2.23 | 0.39 |
| Total Impurities | | 0.51 |

Example 2

Table 2

TABLE 2

| Ingredients | Qty/vial |
|---|---|
| Thiotepa | 100 mg |
| Poloxamer 188 | 10 mg |
| Propylene glycol | 1 ml |
| Ethanol | 9 ml |

Using the ingredients in Table 2, thiotepa was added to a manufacturing vessel containing a mixture of the propylene glycol and ethanol solvents. Poloxamer 188 was added to the mixture and the mixture was stirred to obtain a clear solution. The obtained solution was filtered and filled in vials, followed by capping and sealing of the vials. The formulation was tested for stability at 25° C./60% RH for a period of 7 days. Stability data is summarized in Table 2A.

TABLE 2A

| Stability at Day 7 | RRT | Day 7 |
|---|---|---|
| Purity | | 99.85% |
| Maximum Individual Impurity | 1.36 | 0.15% |
| Total Impurities | | 0.15% |

Example 3

TABLE 3

| Ingredients | Qty/vial |
|---|---|
| Thiotepa | 100 mg |
| Poloxamer 188 | 10 mg |
| Propylene glycol | 5 ml |
| Ethanol | 5 ml |
| NaOH | QS for pH adjustment to 7.5-8.5 |

Using the ingredients in Table 3, thiotepa was added to a manufacturing vessel containing a mixture of propylene glycol and ethanol solvents. Poloxamer 188 was added to the mixture and the mixture was stirred to obtain a clear solution. pH was adjusted to 7.5-8.5 using NaOH. Volume was made up using a mixture of propylene glycol and ethanol solvent. The obtained solution was filtered and filled in vials followed by capping and sealing. The formulation was tested for stability at 25° C./60% RH for a period of 7 days. Stability data is summarized in Table 3A.

TABLE 3A

| Stability at Day 7 | Day 7 |
|---|---|
| Purity | 94.56% |
| Maximum Individual Impurity | 2.06% |
| Total Impurities | 5.44% |

Example 4

TABLE 4

| Ingredients | Qty/vial |
|---|---|
| Thiotepa | 100 mg |
| Poloxamer 188 | 10 mg |
| L-Arginine | 10 mg |
| Propylene glycol | 5 ml |
| Ethanol | 5 ml |
| NaOH | QS for pH adjustment to 7.5-8.5 |

Using the ingredients in Table 4, thiotepa was added to a manufacturing vessel containing a mixture of the solvents. Poloxamer 188 and L-Arginine were added to the mixture and the mixture was stirred to obtain a clear solution. pH was adjusted to 7.5-8.5 using NaOH. Volume was made up using a mixture of propylene glycol and ethanol solvent. The obtained solution was filtered and filled in vials followed by capping and sealing. The formulation was tested for stability at 25° C./60% RH for a period of 7 days. Stability data is summarized in Table 4A.

TABLE 4A

| Stability at Day 7 | Day 7 |
|---|---|
| Purity | 82.25% |
| Maximum Individual Impurity | 16.81% |
| Total Impurities | 17.75% |

Example 5

TABLE 5

| Ingredients | Qty/vial |
|---|---|
| Thiotepa | 100 mg |
| Poloxamer 188 | 10 mg |
| L-Arginine | 10 mg |
| Polyethylene glycol | 5 ml |
| Ethanol | 5 ml |
| NaOH | QS for pH adjustment to 7.5-8.5 |

Using the ingredients in Table 5, thiotepa was added to a manufacturing vessel containing a mixture of the solvents polyethylene glycol and ethanol. Poloxamer 188 and L-Arginine were added to the mixture and the mixture was stirred to obtain a clear solution. pH was adjusted to 7.5-8.5 using NaOH. Volume was made up using a mixture of solvent. The obtained solution was filtered and filled in vials followed by capping and sealing. The formulation was tested for stability at 25° C./60% RH for a period of 7 days. Stability data is summarized in Table 5A.

TABLE 5A

| Stability at Day 7 | Day 7 |
|---|---|
| Purity | 99.93% |
| Maximum Individual Impurity | 0.05% |
| Total Impurities | 0.07% |

Example 6

TABLE 6

| Ingredients | Qty/vial |
|---|---|
| Thiotepa | 100 mg |
| Beta cyclodextrin | 10 mg |
| Propylene glycol | 5 ml |
| Ethanol | 5 ml |

Using the ingredients in Table 6, thiotepa was added to a manufacturing vessel containing a mixture of the solvents propylene glycol and ethanol. Beta cyclodextrin was added to the mixture and the mixture was stirred to obtain a clear solution. The obtained solution was filtered and filled in vials followed by capping and sealing. The formulation was tested for stability at 25° C./60% RH for a period of 7 days. Stability data is summarized in Table 6A.

TABLE 6A

| Stability at Day 7 | Day 7 |
|---|---|
| Purity | 99.07% |
| Maximum Individual impurity | 0.43% |
| Total Impurities | 0.93% |

Example 7

TABLE 7

| Ingredients | Qty/vial |
|---|---|
| Thiotepa | 100 mg |
| Beta cyclodextrin | 10 mg |
| Poloxamer 188 | 10 mg |
| Propylene glycol | 5 ml |
| Ethanol | 5 ml |

Using the ingredients in Table 7, thiotepa was added to a manufacturing vessel containing a mixture of the solvents. Poloxamer 188 and beta cyclodextrin were added to the mixture and the mixture was stirred to obtain a clear solution. The obtained solution was filtered and filled in vials followed by capping and sealing. The formulation was tested for stability at 25° C./60% RH for a period of 7 days. Stability data is summarized in Table 7A.

TABLE 7A

| Stability at Day 7 | Day 7 |
|---|---|
| Purity | 99.09% |
| Maximum Individual impurity | 0.43% |
| Total Impurities | 0.91% |

Instrumentation, Materials and Methods

A High Performance Liquid Chromatograph (HPLC) equipped with gradient module (Shimadzu LC 2010 system or Waters e2695 separation module or equivalent) using LC Solution or Empower Software or equivalent chromatographic software was employed for all experiments. The column employed was a stainless steel column of length 150 mm, internal diameter 4.6 mm filled with porous silica particles of 5.0µ, chemically bonded to octadecyl silane. (GL Sciences, Inc. (Tokyo, Japan) Inertsil® ODS-3V C18 column (150×4.6 mm×5.0µ) or equivalent).

Reagents

Water (MilliQ® (Millipore))

Acetonitrile (HPLC Grade)

Sodium chloride (AR Grade)

Orthophosphoric acid (AR Grade)

Methanol (HPLC Grade)

Ethanol (AR Grade)

Standard: Thiotepa (USP Reference Standard)

Preparation of Mobile Phase A: 100% water filtered through 0.2µ or finer porosity membrane filter.

Preparation of Mobile Phase B: Filtered (through 0.2µ filter) and degassed acetonitrile Chromatographic Parameters:

Flow rate: 1.0 mL/minute

Detection: UV at 215 nm

Injection Volume: 20 µL & 70 µL (for 3500 ppm or 1000 ppm, respectively)

Column oven: 27° C.

Runtime time: 55 minutes.

Rinse solvent: water: acetonitrile (95:05)

The retention time of thiotepa peak is about 15.2 minutes.

TABLE 8

| | Elution Program (Gradient Composition): | |
|---|---|---|
| Time | Mobile phase A (% v/v) | Mobile phase B (% v/v) |
| Initial | 95 | 05 |
| 2.0 | 95 | 05 |
| 10.0 | 80 | 20 |
| 35.0 | 40 | 60 |
| 37.0 | 95 | 05 |
| 55.0 | 95 | 05 |

Preparation of diluent: Mixed ethanol and water in the ratio of 70:30.

Preparation of Resolution solution (To be injected 20 μL only). Accurately weighed and transferred about 10 mg of thiotepa USP reference standard into a 5 ml volumetric flask. Added 2 ml methanol to it and mixed well. Added 50 Lit of 0.1% phosphoric acid solution. Sealed the vial. Heated at 65° C. for 50 seconds. Cooled the solution and added 1.0 mL methanol and mixed well to generate methoxy thiotepa.

Preparation of Standard solution (3.5 ppm; to be injected 20 μL only). Accurately weighed and transferred about 35.0 mg thiotepa USP reference standard into 100 ml volumetric flask. Dissolved in and diluted to volume with diluent & mixed well. Diluted 5 ml of above solution to 50 ml with diluent and mixed well. Further diluted 5 ml of above solution to 50 ml with diluent and mixed well.

Preparation of Sample solution (for 3500 ppm; 20 μLit & for 1000 ppm; 70 μLit). Accurately transferred 0.35 mL of the sample solution into a 1.0 mL volumetric flask, added diluent and mixed well, made up with diluent and mixed well. This preparation is for 3500 ppm solution from 10 mg/mL thiotepa stock solution. Used as such solution in case of 1 mg/mL thiotepa solution (inject 70 μLit).

Preparation of Impurity Identification (Chloro-Ethyl-Analogue) solution (Inject 70 μLit). Accurately weighed and transferred about 15.0 mg of thiotepa USP reference standard into a 20 ml volumetric flask. Added 10 ml water to it and mixed well. Added 1.0 g sodium chloride to it. Boiled the solution in water bath for 10 minutes. Cooled the solution to generates the chloro-ethyl analogue of thiotepa.

Procedure

The following procedures were followed: Separately inject the blank solution, resolution solution, impurity identification solution, standard solution and sample solution into the chromatograph using the given chromatographic parameters and record the chromatograms. Measure the peak responses of thiotepa peak in the chromatogram. Examine the blank chromatogram for any extraneous peak and disregard the corresponding peaks observed in the chromatogram of the sample solution. Any individual unknown impurity which is ≤0.01% obtained by area normalization method is disregarded.

Follow the injection sequence as described in Table 9.

TABLE 9

| | Injection Sequence | |
|---|---|---|
| Sr. no. | Sample | No. of injections |
| 1 | Blank (Diluent) | 1 |
| 2 | Resolution Solution | 1 |
| 3 | Impurity Identification solution | 1 |
| 4 | Standard Solution | 6 |
| 5 | Sample Solution | 1 |

Evaluation of System Suitability

Examine the chromatogram obtained with resolution solution. Resolution between methoxy thiotepa peak and thiotepa peak should be not less than 3.0 The % RSD of area counts of thiotepa peak obtained from six consecutive injections of standard solution should not be more than 2.0%. The Relative Retention Time (RRT) is given in Table 10.

TABLE 10

| Sr. No. | Name of Component | RRT |
|---|---|---|
| 1 | Methoxy Thiotepa | 1.20 |
| 2 | Chloro-Ethyl-Analogue | 1.54 |
| 3 | Thiotepa | 1.00 |

Calculations

Total impurities = % of total known and unknown impurities

Percentage of individual unknown/known impurity =

$$\frac{At}{As} \times \frac{Ws}{100} \times \frac{5}{50} \times \frac{5}{50} \times \frac{\text{Sample Volume}}{\text{Sample Weight}} \times P$$

where,
At: Area counts of known impurity peak obtain from the chromatogram of sample preparation
As: Average area counts of Thiotepa peak obtain from the chromatogram of standard preparation
Ws: Weight of Thiotepa standard taken in mg
P: Potency of Thiotepa standard (% w/w)

Although the formulations, compositions, schemes and methods of the present disclosure have been described with reference to exemplary embodiments thereof, the present disclosure is not limited thereby. Indeed, the exemplary embodiments are implementations of the disclosed methods are provided for illustrative and non-limitative purposes. Changes, modifications, enhancements and/or refinements to the disclosed methods may be made without departing from the spirit or scope of the present disclosure. Accordingly, such changes, modifications, enhancements and/or refinements are encompassed within the scope of the present invention. All publications, patent applications, patents, figures and other references mentioned herein are expressly incorporated by reference in their entirety.

What is claimed is:

1. A ready to use, pharmaceutically acceptable injectable liquid formulation comprising thiotepa or a pharmaceutically acceptable salt thereof and at least one pharmaceutically acceptable solvent or co-solvent, wherein the formulation retains at least 90% of the purity of thiotepa as measured by HPLC after storage at 25° C./60% relative humidity (RH) for a period of 7 days.

2. The formulation of claim 1 wherein the formulation retains at least 94% of the purity of thiotepa as measured by HPLC after storage at 25° C./60% RH for a period of 7 days.

3. The formulation of claim 1 wherein the formulation retains at least 99% of the purity of thiotepa as measured by HPLC after storage at 25° C./60% RH for a period of 7 days.

4. The formulation of claim 3 wherein the formulation retains at least 99% of the purity of thiotepa as measured by HPLC after storage for at least six months at 2-8° C.

5. The formulation of claim 1 comprising ethanol.

6. The formulation of claim 4 comprising ethanol.

7. The formulation of claim 1 comprising ethanol, propylene glycol and optionally one or more of a polymer and a solubilizing agent.

8. The formulation of claim 7 comprising 100 mg thiotepa, 1-10 ml ethanol and 0-5 ml propylene glycol.

9. The formulation of claim 8 comprising 10 ml ethanol and 0 ml propylene glycol.

10. The formulation of claim 7 comprising a polymer.

11. The formulation of claim 7 comprising a solubilizing agent.

12. The formulation of claim 7 comprising a polymer and a solubilizing agent.

13. The formulation of claim 1 consisting essentially of thiotepa and ethanol.

14. The formulation of claim 1 consisting of thiotepa and ethanol.

15. The formulation of claim 1 comprising ethanol, polyethylene glycol (PEG) and optionally one or more of a polymer and a solubilizing agent.

16. The formulation of claim 1 comprising ethanol, polyethylene glycol (PEG), a polymer and a solubilizing agent.

17. The formulation of claim 16 consisting essentially of ethanol, polyethylene glycol (PEG), a polymer, a solubilizing agent, and a pH adjusting component so that the pH of the formulation is from 7.5 to 8.5.

18. The formulation of claim 1 wherein the formulation has a concentration of thiotepa of about 10 mg thiotepa per ml of the total amount of the solvent and/or co-solvent.

19. The formulation of claim 2 wherein the formulation has a concentration of thiotepa of about 10 mg thiotepa per ml of the total amount of the solvent and/or co-solvent.

20. The formulation of claim 3 wherein the formulation has a concentration of thiotepa of about 10 mg thiotepa per ml of the total amount of the solvent and/or co-solvent.

* * * * *

(12) EX PARTE REEXAMINATION CERTIFICATE (12237th)
United States Patent
Kovi et al.

(10) Number: US 11,260,065 C1
(45) Certificate Issued: Mar. 1, 2023

(54) STORAGE-STABLE READY-TO-USE INJECTABLE FORMULATIONS OF THIOTEPA

(71) Applicant: RK Pharma Solutions LLC, Piscataway, NJ (US)

(72) Inventors: Ravishanker Kovi, Monroe Township, NJ (US); George Roby Thomas, Winnipeg (CA); Nirmal Chaitanya Indravadanbhai, Gujarat (IN); Patel Mitesh Manubhai, Gujarat (IN); Thupalli Ajeykumar Reddy, Bangalore (IN); Jayaraman Kannappan, Vadodara (IN)

(73) Assignee: RK PHARMA SOLUTIONS LLC, Piscataway, NJ (US)

Reexamination Request:
No. 90/015,027, May 10, 2022

Reexamination Certificate for:
Patent No.: 11,260,065
Issued: Mar. 1, 2022
Appl. No.: 16/690,696
Filed: Nov. 21, 2019

Related U.S. Application Data

(60) Provisional application No. 62/772,220, filed on Nov. 28, 2018.

(51) Int. Cl.
*A61K 31/675* (2006.01)
*A61K 9/00* (2006.01)

(52) U.S. Cl.
CPC .......... *A61K 31/675* (2013.01); *A61K 9/0019* (2013.01)

(58) Field of Classification Search
None
See application file for complete search history.

(56) References Cited

To view the complete listing of prior art documents cited during the proceeding for Reexamination Control Number 90/015,027, please refer to the USPTO's Patent Electronic System.

*Primary Examiner* — Jerry D Johnson

(57) ABSTRACT

A stable, ready-to-use injectable solution including thiotepa and one or more pharmaceutically acceptable solvents, cosolvents, and/or solubilizing agents. Formulations retain at least 90% and as high as 99% of the purity of thiotepa as measured by HPLC after storage at 25° C./60% RH for a period of 7 days. Certain formulations retain at least 99% of the purity of thiotepa as measured by HPLC after storage for at least six months at 2-8° C.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5, 6, 8, 9 and 18-20 are cancelled.

Claims 1, 7, 15 and 16 are determined to be patentable as amended.

Claims 2-4, 10-14 and 17, dependent on an amended claim, are determined to be patentable.

1. A ready to use, pharmaceutically acceptable injectable liquid formulation comprising thiotepa or a pharmaceutically acceptable salt thereof and [at least one pharmaceutically acceptable solvent or co-solvent] *ethanol,* wherein the formulation retains at least 90% of the purity of thiotepa as measured by HPLC after storage at 25° C./60% relative humidity (RH) for a period of 7 days, *and wherein a ratio of thiotepa to ethanol ranges from 20 mg thiotepa per ml of ethanol to 100 mg thiotepa per ml ethanol.*

7. The formulation of claim 1 *further* comprising [ethanol,] propylene glycol and optionally one or more of a polymer and a solubilizing agent.

15. The formulation of claim 1 *further* comprising [ethanol,] polyethylene glycol (PEG) and optionally one or more of a polymer and a solubilizing agent.

16. The formulation of claim 1 *further* comprising [ethanol,] polyethylene glycol (PEG), a polymer and a solubilizing agent.

* * * * *